(12) United States Patent
Yanagi

(10) Patent No.: US 11,589,883 B2
(45) Date of Patent: Feb. 28, 2023

(54) MEDICAL INSTRUMENT

(71) Applicant: OLYMPUS CORPORATION, Hachioji (JP)

(72) Inventor: Daisuke Yanagi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 346 days.

(21) Appl. No.: 16/840,492

(22) Filed: Apr. 6, 2020

(65) Prior Publication Data

US 2020/0229836 A1 Jul. 23, 2020

Related U.S. Application Data

(63) Continuation of application No. PCT/JP2017/036506, filed on Oct. 6, 2017.

(51) Int. Cl.
*A61B 17/29* (2006.01)
*A61B 17/32* (2006.01)
(Continued)

(52) U.S. Cl.
CPC .. *A61B 17/2909* (2013.01); *A61B 17/320092* (2013.01); *A61B 18/085* (2013.01); *A61B 18/1445* (2013.01); *A61B 18/1447* (2013.01); *A61B 17/072* (2013.01); *A61B 17/32* (2013.01); *A61B 2017/2925* (2013.01);
(Continued)

(58) Field of Classification Search
CPC ............. A61B 17/068; A61B 17/072; A61B 17/07207; A61B 17/28; A61B 17/29; A61B 17/2909; A61B 2017/07214; A61B 2017/07228; A61B 5/0205; A61B 18/1445; A61B 18/1447; A61B 17/32; A61B 2017/00026; A61B 2017/00353;
(Continued)

(56) References Cited

U.S. PATENT DOCUMENTS 5,458,598 A    10/1995  Feinberg et al.
9,089,327 B2 *  7/2015  Worrell ................ A61B 5/0205
(Continued)

FOREIGN PATENT DOCUMENTS

JP    2013-540002 A    10/2013
JP    2014-512904 A    5/2014
(Continued)

OTHER PUBLICATIONS

Apr. 8, 2020 International Preliminary Report on Patentability issued in International Patent Application No. PCT/JP2017/036506.
(Continued)

*Primary Examiner* — Scott A Smith
(74) *Attorney, Agent, or Firm* — Oliff PLC

(57) ABSTRACT

A medical instrument includes a housing, a movable handle, and a spring. The movable handle is configured to move between a first position as an opened position and a second position as a closed position with respect to the housing. The spring is provided between the housing and the movable handle. The spring is configured to apply a biasing force to the housing or the movable handle. The spring is provided to alleviate an increase in the biasing force generated in the spring in response to the movable handle moving from the first position to the second position.

20 Claims, 14 Drawing Sheets

(51) Int. Cl.
  *A61B 18/08* (2006.01)
  *A61B 18/14* (2006.01)
  *A61B 18/00* (2006.01)
  *A61B 17/072* (2006.01)

(52) U.S. Cl.
  CPC .............. *A61B 2017/2929* (2013.01); *A61B 2018/00083* (2013.01); *A61B 2018/00589* (2013.01); *A61B 2018/00601* (2013.01)

(58) Field of Classification Search
  CPC ........ A61B 18/1402; A61B 2018/1412; A61B 2018/00755; A61B 2018/0091
  USPC ...... 227/19, 175.1, 176.1; 606/1, 50, 51, 52, 606/139, 205, 219; 173/170
  See application file for complete search history.

(56) References Cited

U.S. PATENT DOCUMENTS

| | | | |
|---|---|---|---|
| 9,545,253 B2 * | 1/2017 | Worrell | A61B 18/1445 |
| 9,877,720 B2 * | 1/2018 | Worrell | A61B 17/07207 |
| 2013/0030428 A1 | 1/2013 | Worrell et al. | |
| 2013/0345743 A1 * | 12/2013 | Aue | A61B 17/2909 606/205 |
| 2015/0297289 A1 * | 10/2015 | Hirai | A61B 18/1445 606/41 |

FOREIGN PATENT DOCUMENTS

| | | |
|---|---|---|
| JP | 2015-529141 A | 10/2015 |
| JP | 2017-159019 A | 9/2017 |
| WO | 2014/196641 A1 | 12/2014 |

OTHER PUBLICATIONS

Feb. 9, 2021 Office Action issued in Japanese Patent Application No. 2019-546507.
Dec. 26, 2017 International Search Report issued in International Patent Application No. PCT/JP2017/036506.
Sep. 27, 2022 Office Action issued in Chinese Patent Application No. 201780095656.8.

* cited by examiner

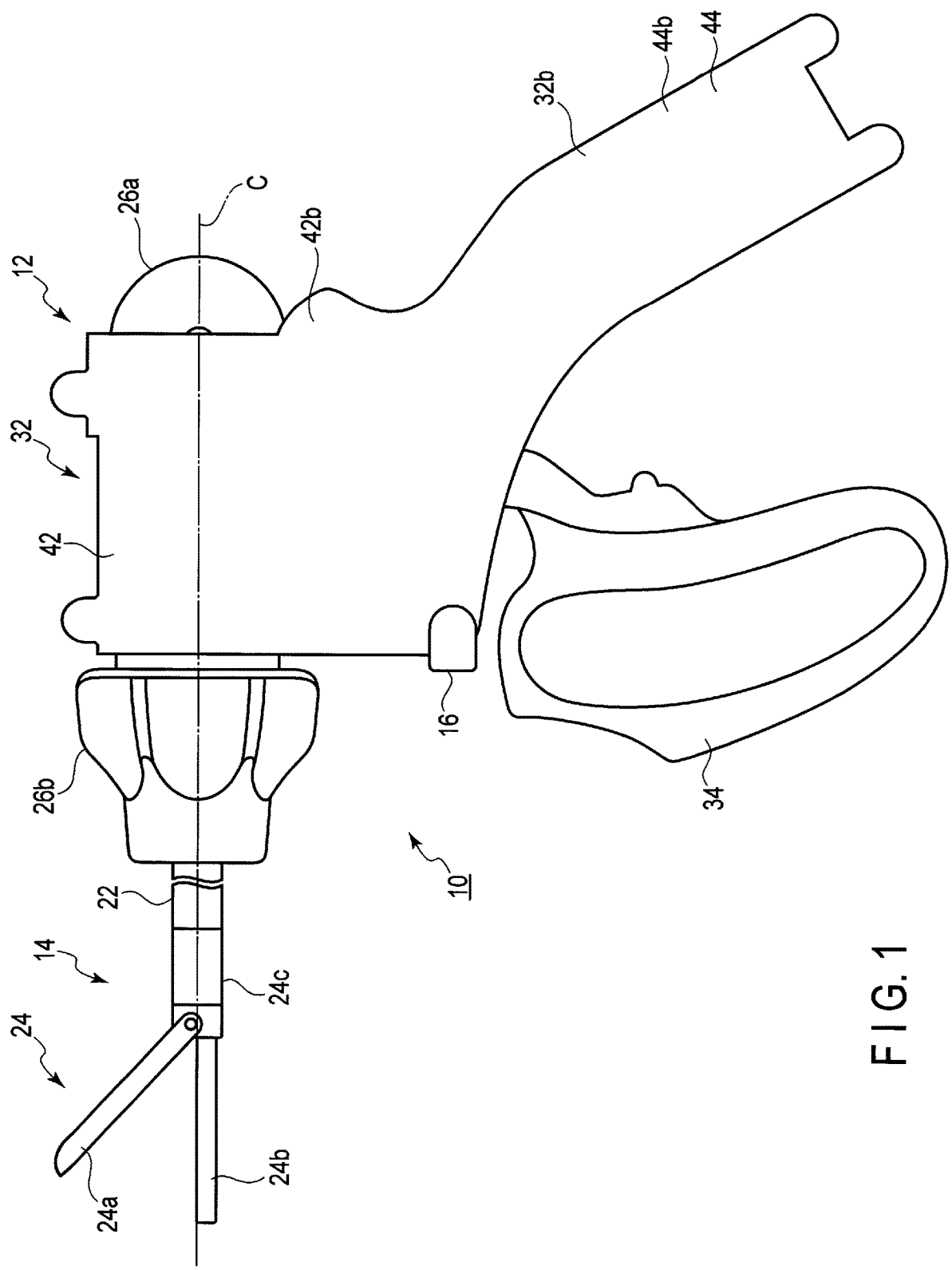
F I G. 1

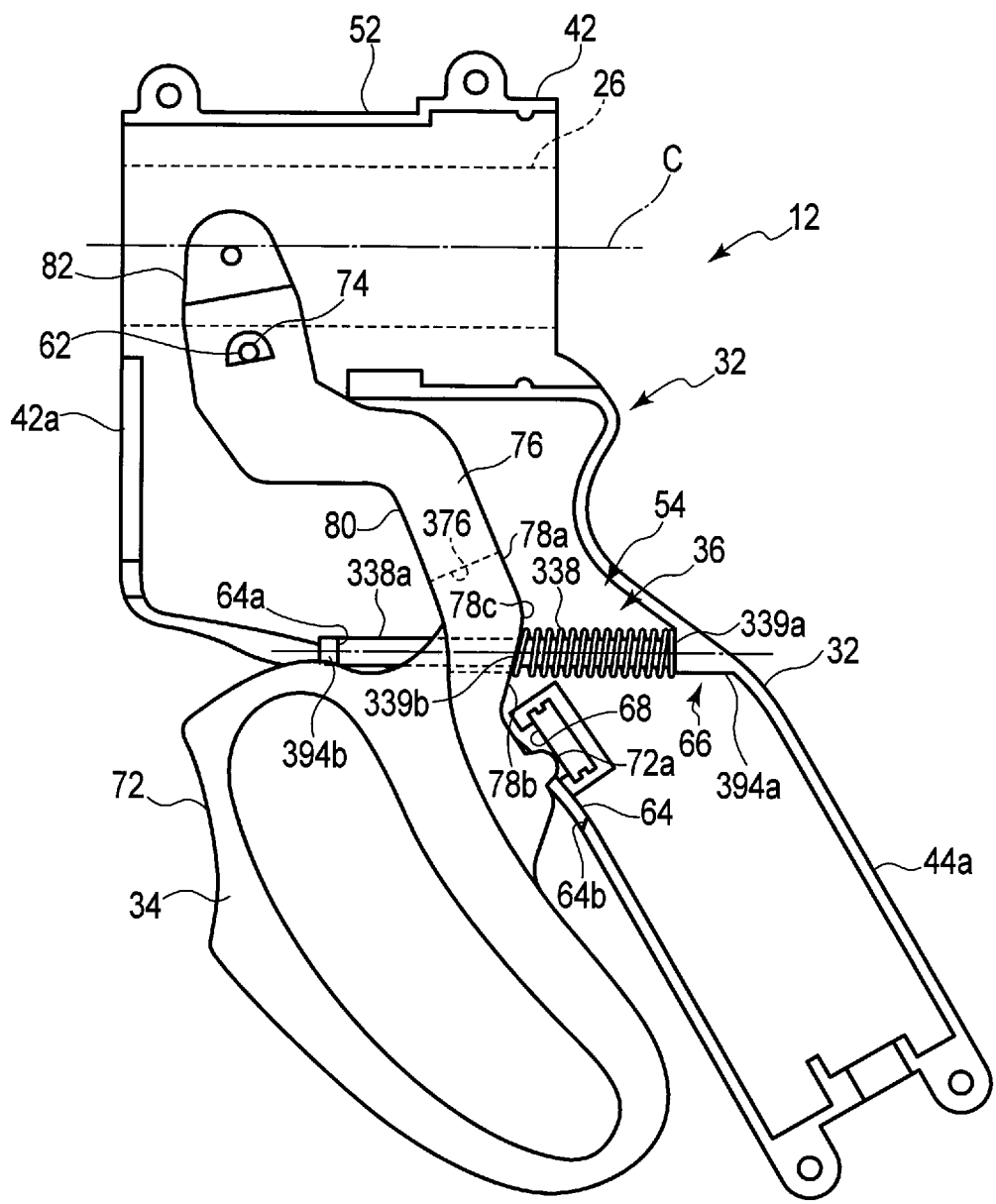
F I G. 10

MEDICAL INSTRUMENT

CROSS-REFERENCE TO RELATED APPLICATIONS

This application is a Continuation Application of PCT Application No. PCT/JP2017/036506, filed Oct. 6, 2017, the entire contents of which are incorporated herein by reference.

BACKGROUND

For example, U.S. Pat. No. 5,458,598A discloses a medical instrument including a movable handle that moves relative to a housing. In this medical instrument, a spring is arranged between the housing and the movable handle. The spring keeps the movable handle away from the housing. A surgeon can move the movable handle to a position close to the housing against a biasing force of the spring.

SUMMARY

Exemplary embodiments relate to a medical instrument including a handle. The medical instrument can include a housing, a movable handle, and a spring. The movable handle is configured to move between a first position as an opened position and a second position as a closed position with respect to the housing. The spring is provided between the housing and the movable handle. The spring is configured to apply a biasing force to the housing or the movable handle. The spring is provided to alleviate an increase in the biasing force generated in the spring in response to the movable handle moving from the first position to the second position.

Advantages will be set forth in the description which follows, and in part will be obvious from the description, or may be learned by practice of the invention. The advantages may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate exemplary embodiments, and together with the general description given above and the detailed description of the embodiments given below, serve to explain the principles of the invention.

FIG. 1 is a schematic view showing a medical instrument according to exemplary embodiments;

FIG. 10 is a schematic view showing a state in which the finger hook portion of the movable handle is brought to a position close to the grip of the housing shown in FIG. 9;

DETAILED DESCRIPTION

Figure 2:
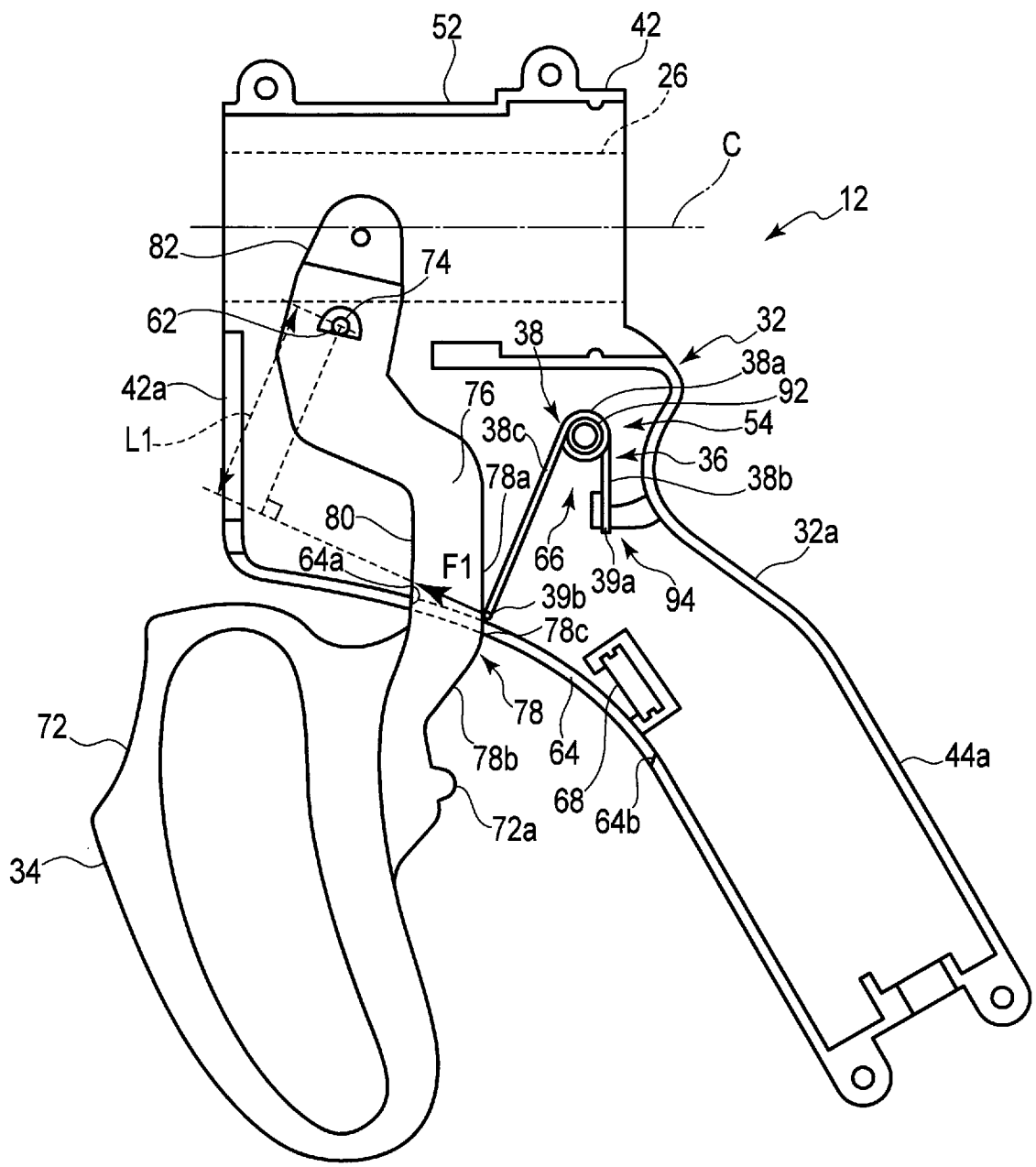
FIG. 2 is a schematic view showing a state in which, while a movable handle and a spring are arranged in a first body of a housing of a handle assembly of the medical instrument according to an exemplary embodiment, a finger hook portion of the movable handle is set apart from a grip of the housing.

Hereinafter, exemplary embodiments will be described with reference to the drawings.

As shown in FIG. 1, a medical instrument 10 includes a handle assembly 12, and a treatment assembly 14 provided in the handle assembly 12.

The treatment assembly 14 includes, for example, a shaft 22 extending from a distal end of the handle assembly 12 toward a distal side, an end effector 24 disposed on the distal side of the shaft 22, and a movement mechanism 26. In the medical instrument 10, a longitudinal axis C of the medical instrument 10 is defined by an extending direction of the shaft 22 with respect to the handle assembly 12. The end effector 24 has a pair of jaws (grasper) 24a and 24b operated by the movement mechanism 26 in response to an operation of a movable handle 34, which will be described later, in the handle assembly 12. FIG. 1 shows an example in which the end effector 24 moves relative to the distal end of the shaft 22 by rotating only one jaw 24a around an axis orthogonal to the longitudinal axis C. The pair of jars 24a and 24b may both move relative to the shaft 22 around the axis orthogonal to the longitudinal axis C.

The medical instrument 10 can be used as a forceps to hold living tissue by the pair of jaws 24a and 24b. Therefore, the jaws 24a and 24b can be open and closed with respect to each other. In addition, the medical instrument 10 can not only grasp the living tissue between the pair of jaws 24a and 24b but also excise the living tissue. The end effector 24 can perform treatment such as coagulation and incision using appropriate treatment energy (e.g., various types of energy such as ultrasonic vibration (ultrasonic energy), high frequency energy, thermal energy, etc.) for the living tissue, for example, in response to an operation of a switch 16 provided in the handle assembly 12 by a publicly-known mechanism between the pair of jaws 24a and 24b. That is, the end effector 24 including the jaws 24a and 24b supplies the treatment energy to the living tissue to perform appropriate treatment at a portion of the living tissue supplied with the energy.

In the example shown in FIG. 1, a bending portion 24c on the distal side of the shaft 22 is bent in response to a rotation operation of an operation element 26a around an axis orthogonal to the longitudinal axis C of the movement mechanism 26 of the handle assembly 12. The operation element 26a or the bending portion 24c may not be present, and an ultrasonic transducer or the like may be used instead of the operation element 26a. In this case, the other jaw 24b of the end effector 24 in FIG. 1 is formed by a part (distal end) of a rod transmitting ultrasonic vibration of longitudinal vibration along the longitudinal axis C from the proximal side to the distal side.

In the example shown in FIG. 1, the end effector 24 rotates around the longitudinal axis C in response to a rotation operation of a rotation knob 26b of the movement mechanism 26 of the handle assembly 12 around the longitudinal axis C. The rotation knob 26b may not be present.

Figure 3:
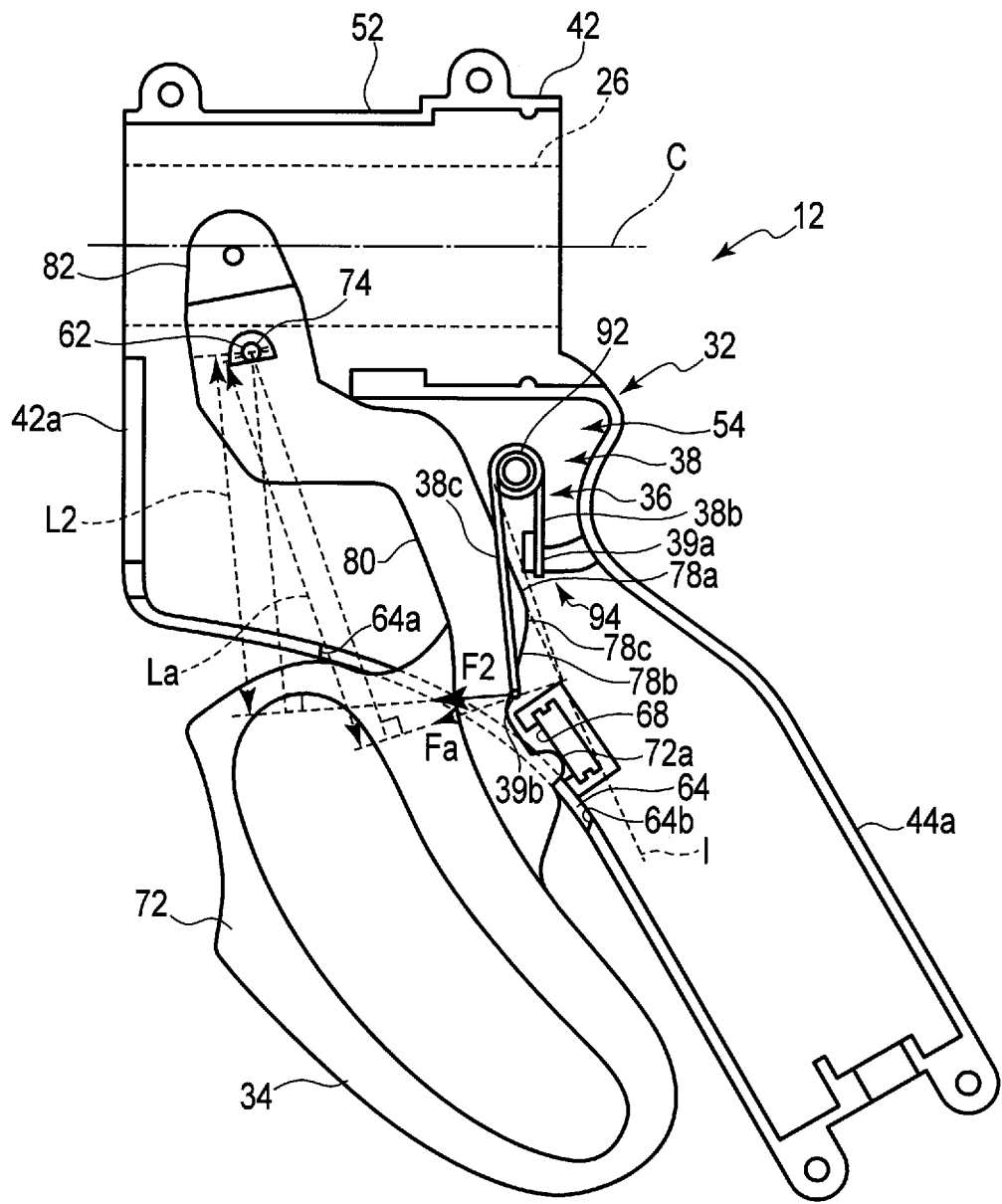
FIG. 3 is a schematic view showing a state in which the finger hook portion of the movable handle is brought to a position close to the grip of the housing shown in FIG. 2.
Figure 4:
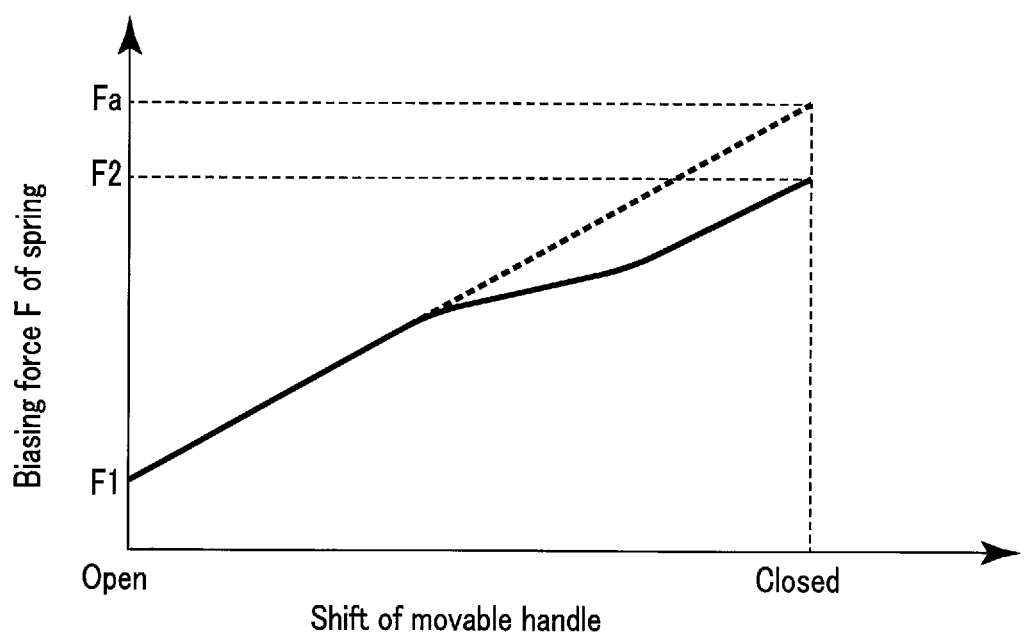
FIG. 4 is a schematic diagram showing a biasing force of the spring of the handle assembly relative to the shifting of the movable handle of the medical instrument according to the first embodiment.

As shown in FIGS. 2 and 3, the handle assembly 12 includes a housing 32, a movable handle 34 that pivots with respect to the housing 32, and a spring 36 that urges the housing 32 and the movable handle 34 away from each other. In the present embodiment, the housing 32 and the movable handle 34 are generally formed into a pistol shape. That is, in the present embodiment, the movable handle 34 is arranged at a position corresponding to a trigger of a pistol with respect to the housing 32. The spring 36 applies a biasing force to the housing 32 or the movable handle 34.

The movable handle 34 is movable relative to the housing 32 between a position shown in FIG. 2 (first position) and a position shown in FIG. 3 (second position). The movable handle 34 includes an operation portion 82 that operates the movement mechanism 26. As an example, when the movable handle 34 is in the first position (open position) shown in FIG. 2, for instance, the jaws 24a and 24b of the end effector 24 shown in FIG. 1 are open because of the operation of the movement mechanism 26 by the operation portion 82. When the movable handle 34 is in the second position (closed position) shown in FIG. 3, for instance, although illustration is omitted, the jaws 24a and 24b of the end effector 24 are closed because of the operation of the movement mechanism 26 by the operation portion 82. As the movable handle 34 shifts from the first position to the second position, the jaws 24a and 24b of the end effector 24 are gradually closed from the opened state.

The housing 32 includes a frame 42 having a longitudinal axis C defined therein, and a fixed handle (grip) 44 extending from the frame 42.

The housing 32 and the movable handle 34 are formed of, for example, an electrically insulating resin material. The housing 32 is formed by, for example, fixing two divided bodies (first body 32a and second body 32b (see FIG. 1)) having electrical insulating properties by a suitable combination of fitting, screw fixing, etc. Therefore, in use of the medical instrument 10, as shown in FIG. 1, a later-described rotation support point portion 74 and operation portion 82 of the movable handle 34 as well as the spring 36 are arranged inside the housing 32 of the two bodies (first body 32a and second body 32b).

The first body 32a includes a first half frame (first divided frame) 42a, and a first half grip (first divided grip) 44a. In the examples shown in FIGS. 2 and 3, the first half frame 42a and the first half grip 44a are integrally formed. The second body 32b has a shape that prevents an arrangement portion 54, which will be described later, of the first half frame 42a and the first half grip 44a from being exposed. It is preferable that the outer surface of the second body 32b is formed symmetrical to the first body 32a with a plane (virtual plane) including the longitudinal axis C as a symmetry plane. In the second body 32b shown in FIG. 1, it is preferable that a second half frame 42b and a second half grip 44b are integrated.

The first half frame 42a includes a first main body (a first divided main body) 52 having a half-pipe shape in which the movement mechanism 26 of the end effector 24 is arranged, and a concave arrangement portion 54 in which the movable handle 34 and the spring 36 are arranged.

The arrangement portion 54 includes a rotation shaft 62 that supports the movable handle 34, a concave groove 64 that defines a movable range of the movable handle 34, and a spring support portion 66 in which the spring 36 is arranged. It is preferable that the rotation shaft 62 is orthogonal to the longitudinal axis C. The movable handle 34 pivots around the rotation shaft 62. The movable handle 34 moves along a virtual plane of motion, for example, including a longitudinal axis C, and formed when the movable handle 34 moves between the first position and the second position with respect to the housing 32. The movable handle 34 is pivotable within a predetermined range between a first edge 64a and a second edge 64b of the concave groove 64.

Here, the rotation shaft 62 of the movable handle 34 is supported by the arrangement portion 54, but the rotation shaft 62 may be supported by the half-pipe shape main body 52. That is, the rotation shaft 62 may be supported by any portion of the first half frame 42a. The rotation shaft 62 of the first body 32a of the housing 32 cooperates with the second body 32b of the housing 32 to prevent the movable handle 34 from slipping out of the housing 32 during use of the medical instrument 10.

In the present embodiment, the arrangement portion 54 includes, at a position adjacent to the concave groove 64, a contact portion 68 with which a protrusion 72a, which will be described later, on the rear surface (surface on the proximal side) of the movable handle 34 comes into contact. A contact surface 80, which will be described later, on the front surface (surface on the distal side) of the movable handle 34 is in contact with the first edge 64a of the concave groove 64. The protrusion 72a on the rear surface of the movable handle 34 is brought into contact with the contact portion 68 before the protrusion 72a of the movable handle 34 is brought into contact with the second edge 64b of the concave groove 64. Therefore, the movable range of the movable handle 34 is defined between the first edge 64a of the concave groove 64 and the contact portion 68.

The movable handle 34 includes a finger hook portion 72 around which a surgeon hooks a finger, a rotation support point portion 74 supported by the rotation shaft 62, and a connecting portion 76 provided between the rotation support point portion 74 and the finger hook portion 72. On the rear surface of the movable handle 34, the protrusion 72a brought into contact with the contact portion 68 is formed.

The connecting portion 76 includes a support surface (contact surface) 78 on which an end portion (second end portion) 39b, which will be described later, of the spring 36 is supported, and a contact surface 80 which is urged toward a state of being in contact with the first edge 64a of the concave groove 64 of the first half frame 42a by the action of the spring 36. In the present embodiment, the support surface 78 is formed on the rear surface of the connecting portion 76, while the contact surface 80 is formed on the front surface of the connecting portion 76. The support surface (contact surface) 78 intersects the plane of notion on which the movable handle 34 moves.

The support surface 78 is formed as a substantially V-shaped curved surface as a whole. The support surface 78 includes, for example, a planar surface (first inclined surface) 78a, and an inclined surface (second inclined surface) 78b relative to the planar surface 78a. The planar surface (first region) 78a is located closer to the rotation shaft 62 and the rotation support point portion 74. The inclined surface (third region) 78b is located farther away than the planar surface 78a with respect to the rotation shaft 62 and the rotation support point portion 74. A curved surface (second region) 78c is formed between the planar surface 78a and the inclined surface 78b to allow for smooth connection between them. The curved surface (second region) 78c is located farther away, with respect to the rotation shaft 62 and the rotation support point portion 74, than the planar surface 78a, and closer than the inclined surface 78b.

For example, the normal direction of the planar surface 78a is directed to the proximal side along the longitudinal axis C in FIG. 2. The normal direction of the inclined surface 78b is directed toward the distal end side of the first half grip 44a away from the first body 52 in FIG. 2.

For simplicity of illustration, it is assumed that the planar surface 78a is orthogonal or substantially orthogonal to the longitudinal axis C when movable handle 34 is in the first position. The inclined surface 78b is brought to a position close to a state of being orthogonal or substantially orthogonal to the longitudinal axis C when the movable handle 34 is in the second position compared to the first position. The end portion 39b of the spring 36 continues to be in contact with the support surface 78 (planar surface 78a, inclined surface 78b, or curved surface 78c) in accordance with the position of the movable handle 34.

The contact surface 80 of the connecting portion 76 is in contact with the first edge 64a of the concave groove 64 of the first half frame 42a when the movable handle 34 is in the first position as shown in FIG. 2 with respect to the housing 32. When the movable handle 34 moves from the first position shown in FIG. 2 toward the second position shown in FIG. 3 with respect to the housing 32, the contact surface 80 of the connecting portion 76 is separated from the first edge 64a of the concave groove 64. At this time, the end portion 39b, which will be described later, of the spring 36 is a free end, and while sliding with respect to the support surface 78, continuously applies to the connecting portion 76 a biasing force causing the contact surface 80 of the movable handle 34 to move to the first edge 64a of the concave groove 64 of the first half frame 42a. Therefore, the biasing force against the movable handle 34 by the spring 36 is continuously applied to the distal side with respect to the housing 32.

In the medical instrument 10 according to the present embodiment, a torsion spring 38 is included as a spring 36 between the first body 32a of the housing 32 and the movable handle 34. The torsion spring 38 includes a coil 38a, a first arm 38b, and a second arm 38c. The first arm 38b and the second arm 38c extend from the coil 38a. Here, the second arm 38c is formed longer than the first arm 38b. The end portion (first end portion) 39a of the first arm 38b or its vicinity is supported by a support portion 94 which will be described later.

The end portion (second end portion) 39b of the second arm 38c is formed into a substantial L shape. As shown in FIG. 3, the second arm 38c is closer to the second body 32b than a side surface 84 on a side which is closer to the second body 32b of the connecting portion 76. By virtue of the end portion 39b being bent, the second arm 38c is brought into contact with the support surface 78 on the rear surface of the connecting portion 76 by the biasing force pushing toward the front surface side.

The first body 32a includes a spring support portion 66 that supports the spring 36. The spring support portion 66 has a boss 92 that supports the coil 38a of the torsion spring 38, and a support portion 94 that supports the first arm 38b. The first arm 38b and the second arm 38c of the torsion spring 38 are disposed between the first body 32a of the housing 32 and the movable handle 34 at an opening angle smaller than the natural opening angle. The support portion 94 may support the end portion 39a of the first arm 38b of the torsion spring 38 as a free end or as a fixed end.

The boss 92 and the support portion 94 of the first body 32a of the housing 32 cooperate with the second body 32b of the housing 32 to prevent the torsion spring 38 from slipping out of the spring support portion 66 during use of the medical instrument 10.

Next, advantageous effects of the medical instrument 10 according to the present embodiment will be described with reference to FIGS. 1 to 4.

The medical instrument 10 is used, for example, in an assembled manner as shown in FIG. 1. A surgeon (operator) such as a doctor using the medical instrument 10, for example, places a thumb or a palm of one hand (right or left) on the rear of the fixed handle 44, and hooks fingers around the finger hook portion 72 of the movable handle 34 with a middle finger, ring finger, little finger, etc. of the same hand. The surgeon appropriately moves the movable handle 34 relative to the fixed handle 44 between the first position shown in FIGS. 1 and 2 and the second position show in FIG. 3 to bring the end effector 24 of FIG. 1 into an appropriate state.

The end portion 39b of the second arm 38c of the torsion spring 38 is in contact with the support surface 78 of the movable handle 34. As show in FIG. 4, when the movable handle 34 is in the first position, biasing force F1 (>0) of the torsion spring 38 acts on the support surface 78 of the movable handle 34. As an example, the direction of the biasing force F1 in FIG. 2 is a direction orthogonal to the second arm 38c of the torsion spring 38. Therefore, when the movable handle 34 is in the first position, the end portion 39b of the torsion spring 38 urges the contact surface 80 of the movable handle 34 toward the state of being in contact with the first edge 64a of the concave groove 64.

When moving the movable handle 34 from the first position to the second position, the surgeon moves the movable handle 34 against the biasing force F1 of the torsion spring 38.

When the movable handle 34 is in or near the first position, the end portion 39b of the torsion spring 38 is in contact with the planar surface 78a of the support surface 78 of the connecting portion 76 of the movable handle 34. When the movable handle 34 is in the first position, the planar surface 78a is in the state of being orthogonal or substantially orthogonal to the longitudinal axis C. When the surgeon moves the movable handle 34 from the first position to the second position, the positions of the coil 38a and the first arm 38*b* of the torsion spring 38 do not change. Therefore, as the movable handle 34 moves from the first position to the second position, the end portion 39*b* of the second arm 38*c* comes closer to the first arm 38*b* while sliding from the planar surface 78*a* toward the curved surface 78*c* and being in contact. Therefore, as show in FIG. 4, the biasing force F of the torsion spring 38 increases in a linear or substantially linear manner.

As the movable handle 34 moves from the first position show in FIG. 2 to the second position show in FIG. 3, the contact position of the end portion 39*b* of the second arm 38*c* of the torsion spring 38 with respect to the support surface 78 changes (shifts). As the movable handle 34 moves from the first position to the second position, the end portion 39*b* of the torsion spring 38 slides from the planar surface (first region) 78*a* toward the inclined surface (third region) 78*b* through the curved surface (second region) 78*c*.

In FIG. 2, the normal direction of the inclined surface 78*b* is directed toward the distal end side of the first half grip 44*a* away from the first body 52. In FIG. 3, the normal direction of the inclined surface 78*b* is brought closer to a state of being parallel to the longitudinal axis C. Even when the protrusion 72*a* of the movable handle 34 is in a state of being brought into contact with the contact portion 68 of the housing 32, the normal direction of the inclined surface 78*b* is between a state of being parallel to the longitudinal axis C and a state of being directed toward the distal end side away from the first body 52. Therefore, in response to the movable handle 34 moving from the first position to the second position, the contact position between the end portion 39*b* of the torsion spring 38 and the support surface 78 of the movable handle 34, particularly when at the curved surface 78*c* and the inclined surface 78*b*, moves relative to a side where the biasing force is applied to the movable handle 34 (front surface side of the handle assembly 12). That is, the contact position between the end portion 39*b* of the torsion spring 38 and the support surface 78 of the movable handle 34 shifts to the side where the biasing force is applied (front surface side of the handle assembly 12) in comparison to a position indicated by dashed line I obtained by virtually extending the planar surface 78*a* of the support surface 78. The inclined surface (contact surface) 78*b* of the movable handle 34 is inclined so as to shift the end portion 39*b* of the second arm 38*c* to the side where the biasing force is applied to the movable handle in response to the movable handle 34 moving from the first position to the second position. Therefore, when the end portion 39*b* of the torsion spring 38 slides along the inclined surface 78*b*, an increase in the biasing force exerted by the end portion 39*b* of the torsion spring 38 is suppressed as compared to when the planar surface 78*a* is continuous as indicated by the dashed line I.

When the movable handle 34 is in the second position, the end portion 39*b* of the torsion spring 38 maintains a state of urging the movable handle 34 toward the first edge 64*a* of the concave groove 64. Biasing force F2 of the torsion spring 38, obtained when the movable handle 34 is in the second position as shown in FIG. 3, is smaller than biasing force Fa obtained when the support surface 78 of the connecting portion 76 is formed only by the planar surface. Therefore, in the present embodiment, when the movable handle 34 moves from the first position to the second position, the biasing force F of the torsion spring 38 is reduced rather than linearly increased. Thus, the surgeon using the medical instrument 10 according to the present embodiment requires a reduced force when maintaining a state of gripping the movable handle 34.

Here, as shown in FIG. 2, the biasing force F1 at the end portion 39*b* of the torsion spring 38 in the direction orthogonal to the second arm 38*c*, and distance L1 of the movable handle 34 from the rotation shaft 62 to a position orthogonal to the direction of the biasing force F1 (direction orthogonal to the extending direction of the second arm 38*c*), are set. At the first position, moment (grip force amount) M1 of force around the axis of the rotation shaft 62 can be expressed as M1=F1dL1.

As shown in FIG. 3, the biasing force F2 at the end portion 39*b* of the torsion spring 38 in the direction orthogonal to the second arm 38*c*, and distance L2 of the movable handle 34 from the rotation shaft 62 to a position orthogonal to the direction of the biasing force F2 (direction orthogonal to the extending direction of the second arm 38*c*), are set. At the second position, moment (grip force amount) M2 of force can be expressed as M2=F2dL2. At this time, the biasing force F1 is smaller than the biasing force F2, while the distance L1 is smaller than the distance L2. Therefore, the moment M of the force around the axis of the rotation shaft 62 may increase from the first position toward the second position.

As shown in FIG. 3, when it is assumed that the support surface 78 is formed only by the planar surface, virtual biasing force Fa of the torsion spring 38 in a direction orthogonal to the second arm 38*c*, and distance La of the movable handle 34 from the rotation shaft 62 to a position orthogonal to the biasing force Fa, are set. When the support surface 78 is formed only by the planar surface, moment (grip force amount) Ma of virtual force can be expressed as Ma=FadLa. At this time, the biasing force F2 is smaller than the biasing force Fa, while the distance L2 is smaller than the distance La. Therefore, the moment M2 of the force around the axis of the rotation shaft 62 is smaller than the moment Ma.

Accordingly, the grip force amount required by the surgeon may increase from the first position toward the second position, but in the vicinity of the second position, a biasing force is applied from the end portion 39*b* of the second arm 38*c* of the torsion spring 38 to the inclined surface 78*b*, not to the planar surface 78*a*. Therefore, the surgeon can perform the operation of gripping the movable handle 34 relative to the fixed handle 44 with a lower force (force amount) compared to when it is assumed that the support surface 78 is formed only by the planar surface. Therefore, according to the present embodiment, it is possible to provide a medical instrument 10 in which a surgeon can easily perform the gripping operation of the movable handle 34 while the spring 36 keeps the movable handle 34 away from the housing 32 by means of the biasing force.

As the movable handle 34 moves from the first position to the second position in accordance with the contact position of the end portion 39*b* of the second arm 38*c* with respect to the support surface 78 of the connecting portion 76 described in the present embodiment, the biasing force F of the torsion spring 38 may increase in a substantially linear manner at a position close to the first position, whereas the biasing force F less increases at a position close to the second position as compared to when it rises in a substantially linear manner. Therefore, in the medical instrument 10 according to the present embodiment, the force required when the surgeon grips the movable handle 34 from the first position to the second position can be lowered than when the biasing force F of the torsion spring 38 increases in a substantially linear manner.

Therefore, when the movable handle 34 moves from the first position to the second position, the force required when the surgeon grips the movable handle 34 from the first position to the second position can be adjusted by reducing a contact region of the planar surface (first inclined surface) 78a to the end portion 39b of the torsion spring 38, increasing a contact area of the inclined surface (second inclined surface) 78b, and appropriately adjusting an angle between the planar surface 78a and the inclined surface 78b.

When the surgeon grips the movable handle 34 with respect to the fixed handle 44 and shifts the position of the movable handle 34 from the first position to the second position, the living tissue of the treatment object is grasped between the pair of jaws 24a and 24b of the end effector 24. When the surgeon performs a pressing operation of the switch 16 in this state, treatment such as coagulation, incision and the like is performed on the living tissue by appropriate treatment energy (e.g., various types of energy such as ultrasonic vibration, high frequency energy, thermal energy, etc.). The surgeon releases the grip of the movable handle 34 with respect to the fixed handle 44 and shifts the position of the movable gripping the movable handle 34 with respect to the fixed handle 44 can be lowered as compared to when the biasing force F of the torsion spring 38 increases in a substantially linear manner. Therefore, the surgeon can easily perform treatment repeatedly using the medical instrument 10.

When the surgeon presses the switch 16 to apply an appropriate energy to the living tissue, the surgeon maintains the movable handle 34 in a state of being disposed in the second position (a state in which the movable handle 34 is gripped with respect to the fixed handle 44). At this time, the surgeon needs to continuously exert a force F greater than the force F2. On the other hand, the force F2 is smaller than the force Fa. Therefore, the surgeon can maintain the movable handle 34 in the second position with the force F smaller than the force Fa.

As shown in FIGS. 2 and 3, the support surface 78 is formed by the planar surface 78a, the curved surface 78c and the inclined surface 78b, but it is also preferable to form it by a curved surface alone.

The boss 92 of the spring support portion 66 is arranged in the arrangement portion 54 of the frame 42, but it may also be arranged in the first half grip 44a of the fixed handle 44 by appropriately forming the shape of the support surface 78.

Next, another exemplary embodiment will be described with reference to FIGS. 5A to 6B. The movable gripping the movable handle 34 with respect to the fixed handle 44 can be lowered as compared to when the biasing force F of the torsion spring 38 increases in a substantially linear manner. Therefore, the surgeon can easily perform treatment repeatedly using the medical instrument 10.

When the surgeon presses the switch 16 to apply an appropriate energy to the living tissue, the surgeon maintains the movable handle 34 in a state of being disposed in the second position (a state in which the movable handle 34 is gripped with respect to the fixed handle 44). At this time, the surgeon needs to continuously exert a force F greater than the force F2. On the other hand, the force F2 is smaller than the force Fa. Therefore, the surgeon can maintain the movable handle 34 in the second position with the force F smaller than the force Fa.

As shown in FIGS. 2 and 3, the support surface 78 is formed by the planar surface 78a, the curved surface 78c and the inclined surface 78b, but it is also preferable to form it by a curved surface alone.

The boss 92 of the spring support portion 66 is arranged in the arrangement portion 54 of the frame 42, but it may also be arranged in the first half grip 44a of the fixed handle 44 by appropriately forming the shape of the support surface 78.

Next, another exemplary embodiment will be described with reference to FIGS. 5A to 6B. The movable handle 34 is movable between the first position shown in FIGS. 5A and 5B and the second position shown in FIGS. 6A and 6B.

An example of using the torsion spring 38 as the spring 36 will be described.

The spring support portion 66 of the arrangement portion 54 of the housing 32 includes a rod 192 and a support portion 194. The rod 192 supports a coil 38a of the torsion spring 38 to be movable along the longitudinal axis of the rod 192. The support portion 194 supports a first arm 38b, for example, to be rotatable around an axis X orthogonal to the longitudinal axis C. Here, the first arm 38b maintains the positional relationship with the support portion 194 by slip prevention 194a shown in FIGS. 5B and 6B.

The rod 192 extends in a state of being orthogonal to the longitudinal axis C, or in a state of being inclined with respect to the longitudinal axis C and a direction orthogonal to the longitudinal axis C. The rod 192 may be non-parallel to the longitudinal axis C. Here, the rod 192 is described as being inclined with respect to the longitudinal axis C and the direction orthogonal to the longitudinal axis C, and extending from a position close to the main body 52 toward the second body 32b of the arrangement portion 54 of the first body 32a of the housing 32. One end of the rod 192 is supported by the first body 32a, while the other end of the rod 192 is supported by the second body 32b. In the present embodiment, compared to the support position of the first body 32a of one end of the rod 192, the support position of the second body 32b of the other end of the rod 192 is located on the forward side along the longitudinal axis C.

The connecting portion 76 includes a first inclined surface 178a and a second inclined surface (contact surface) 178b. The first inclined surface 178a is formed at a position closer to the rotation shaft 62 and the rotation support point portion 74 than the second inclined surface 178b. The first inclined surface 178a and the second inclined surface 178b nay be planar surfaces, curved surfaces, or a combination of planar and curved surfaces.

The first inclined surface 178a and the second inclined surface 178b are each inclined with respect to the longitudinal axis C. The first inclined surface 178a and the second inclined surface 178b are inclined with respect to the rotation shaft 62 and the rotation support point portion 74. In the first inclined surface 178a, the proximal side along the longitudinal axis C is closer to the arrangement portion 54 of the first body 32a as compared to the distal side. In the second inclined surface 178b, the proximal side along the longitudinal axis C is closer to the arrangement portion 54 of the first body 32a as compared to the distal side. The inclination angle of each of the first inclined surface 178a and the second inclined surface 178b relative to the longitudinal axis C is set appropriately.

The first inclined surface 178a is provided with a concave groove 178c in which the rod 192 is guided (extracted and inserted). It is preferable that the concave groove 178c has a width through which the rod 192 passes but the coil 38a does not pass. The coil 38a of the torsion spring 38 is slidable on the first inclined surface 178a. The end portion 39b of the second arm 38c of the torsion spring 38 is slidable on the second inclined surface 178b.

When the movable handle 34 is in the first position, the first arm 38b and the second arm 38c of the torsion spring 38 are disposed between the support portion 194 of the first body 32a of the housing 32 and the second inclined surface 178b of the movable handle 34 at an opening angle smaller than the natural opening angle.

Next, advantageous effects of the medical instrument 10 according to the present embodiment will be described with reference to FIGS. 5A to 6B. The medical instrument 10 is used in a manner similar to that described in the first embodiment.

The end portion 39b of the second arm 38c of the torsion spring 38 is in contact with the second inclined surface 178b of the movable handle 34. When the movable handle 34 is in the first position, the end portion 39b of the torsion spring 38 presses (urges) the second inclined surface 178b. Therefore, the torsion spring 38 urges the contact surface 80 of the movable handle 34 toward a state of being in contact with the first edge 64a of the concave groove 64 by a component (hereinafter referred to as a biasing force F1) in a later-described direction of the biasing force exerted by the end portion 39b of the second arm 38c relative to the second inclined surface 178b. Therefore, when the movable handle 34 is in the first position, the contact surface 80 of the movable handle 34 is maintained in contact with the first edge 64a of the concave groove 64 of the housing 32.

When the movable handle 34 moves from the first position to the second position, the surgeon moves the movable handle 34 against the biasing force F1 of the torsion spring 38.

Figure 5A:
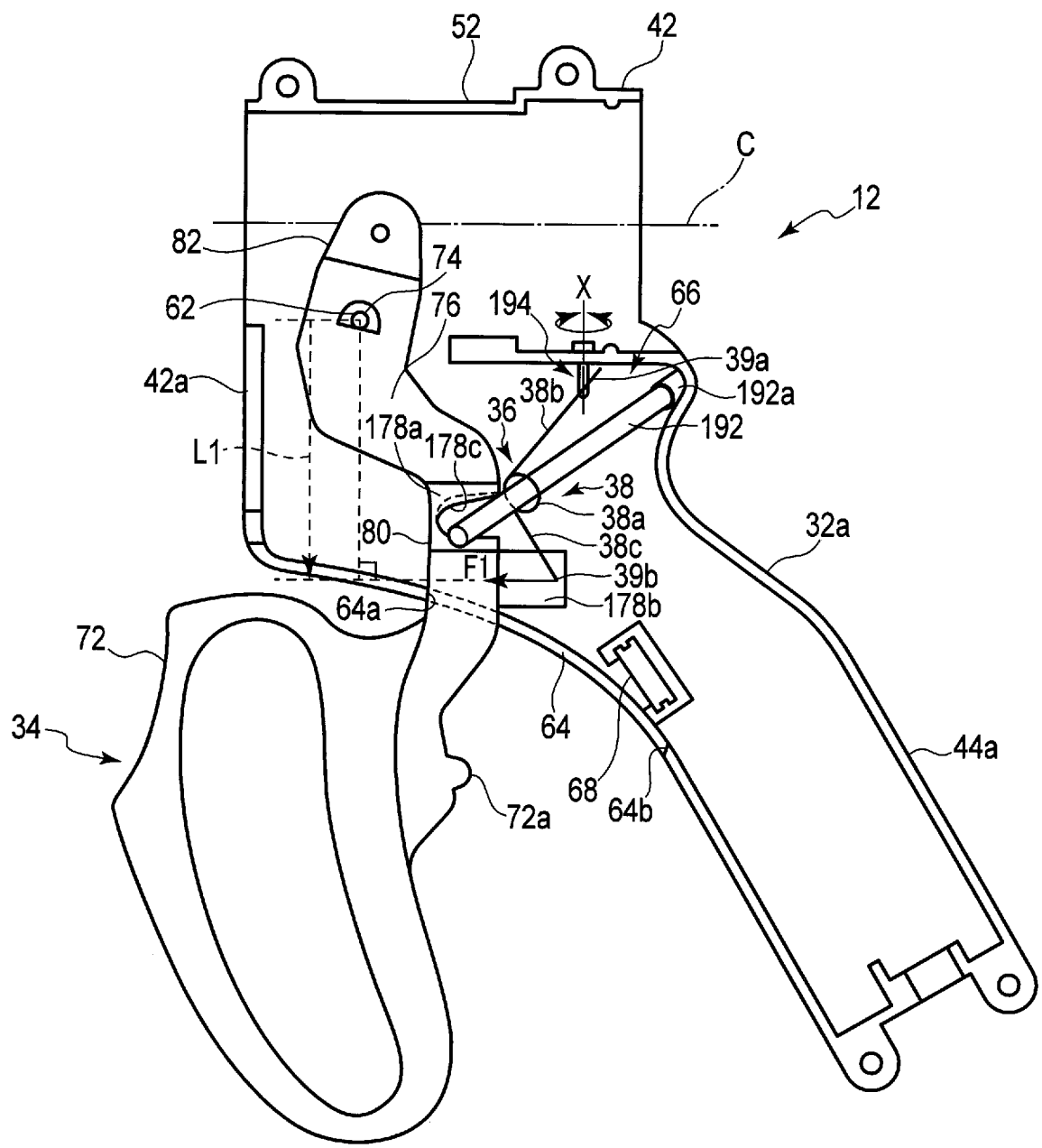
FIG. 5A is a schematic view showing a state in which, while a movable handle and a spring are arranged in a first body of a housing of a handle assembly of a medical instrument according to an exemplary embodiment, a finger hook portion of the movable handle is set apart from a grip of the housing.
Figure 5B:
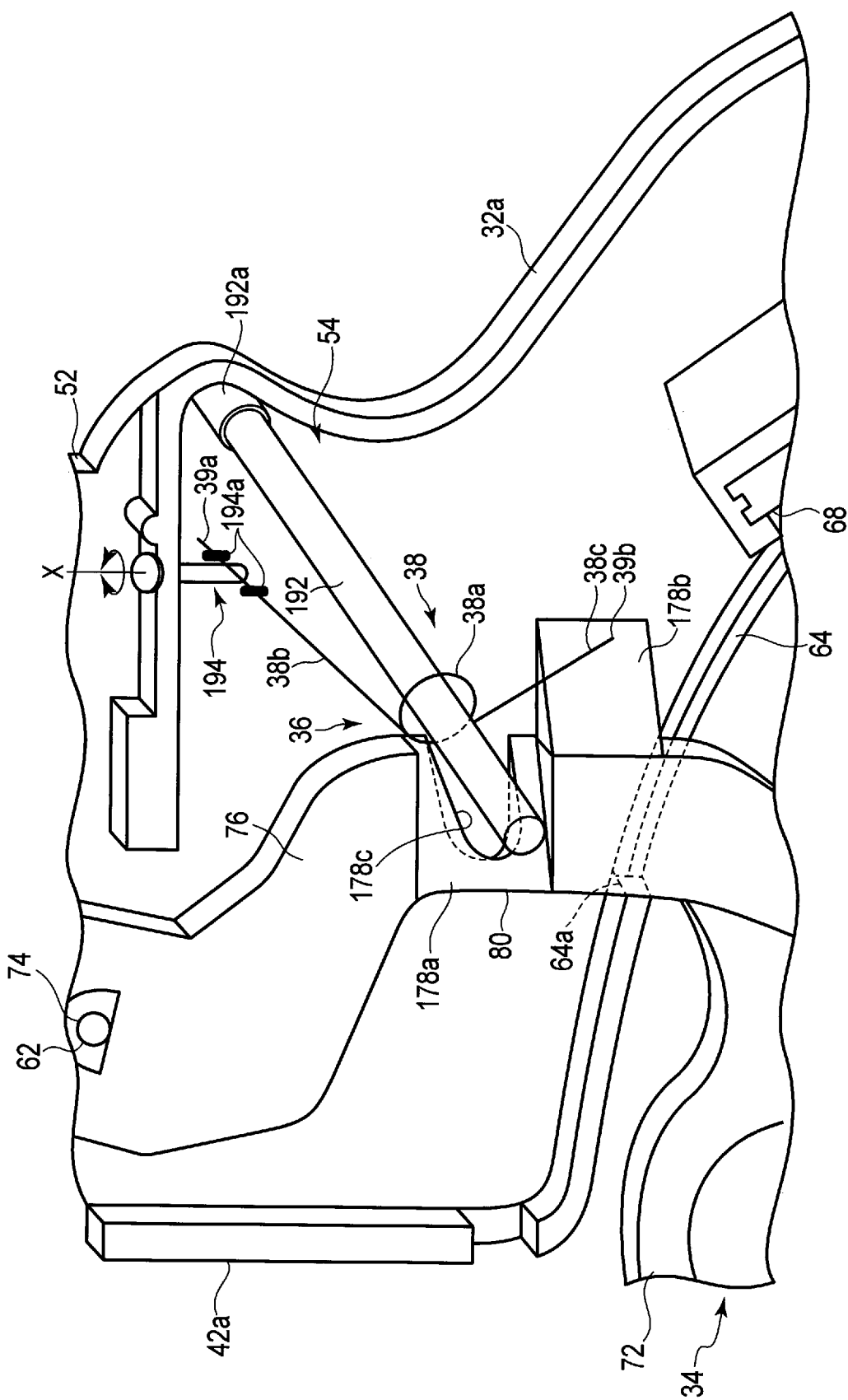
FIG. 5B is a schematic perspective view showing, in an enlarged manner, a connecting portion and the spring of the movable handle shown in FIG. 5A.
Figure 6A:
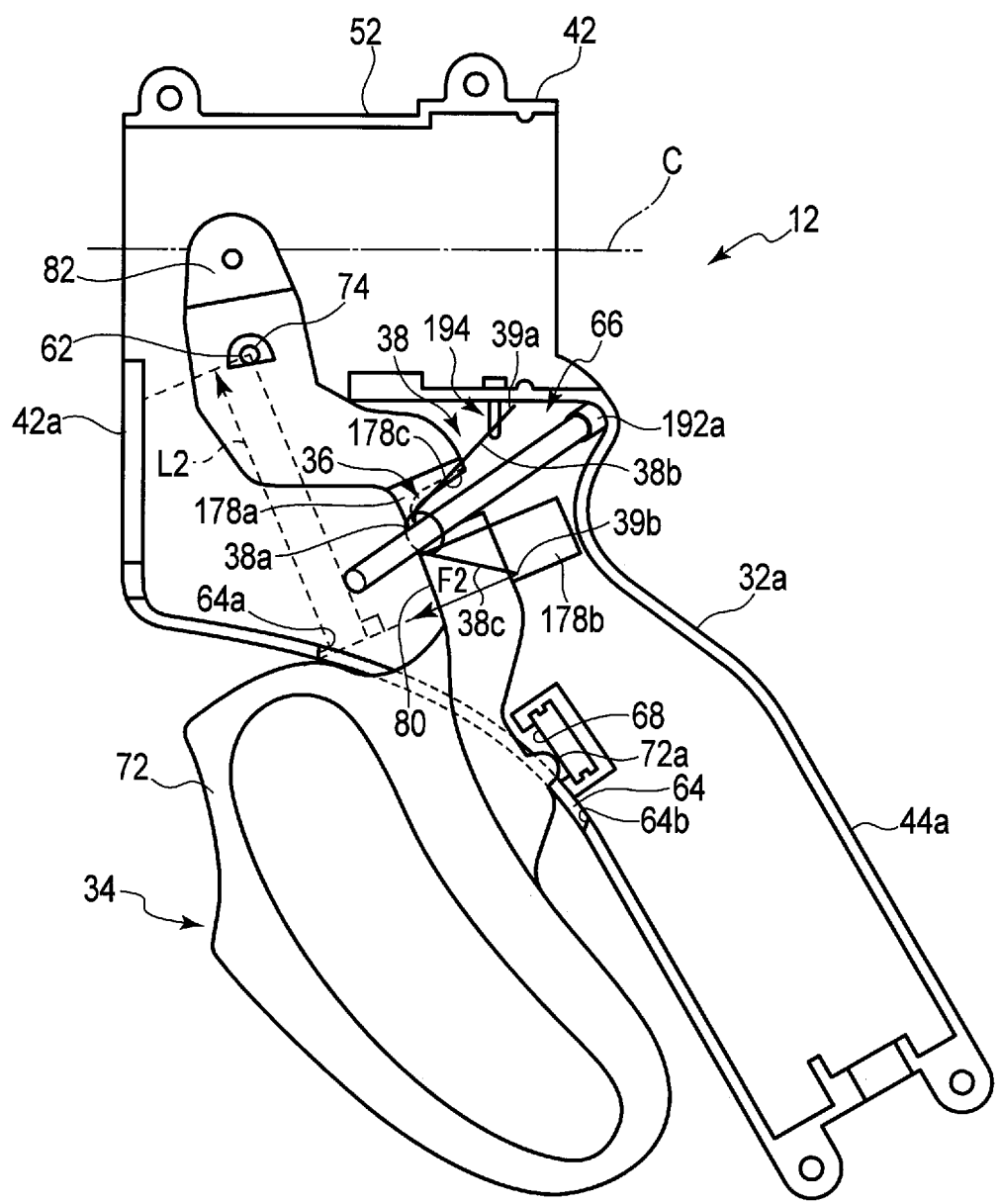
FIG. 6A is a schematic view showing a state in which the finger hook portion of the movable handle is brought to a position close to the grip of the housing shown in FIG. 5A.
Figure 6B:
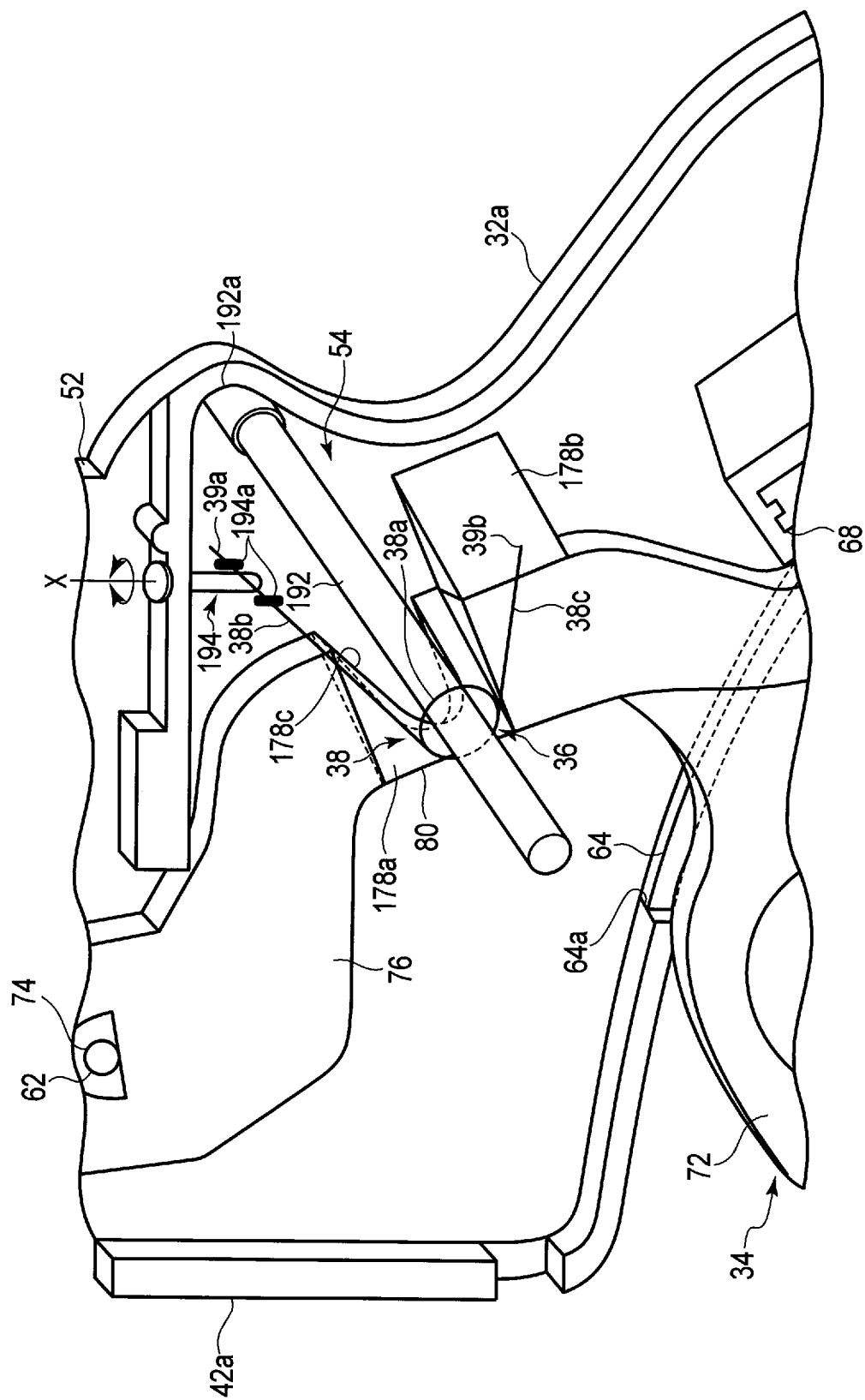
FIG. 6B is a schematic perspective view showing, in an enlarged manner, the connecting portion and the spring of the movable handle shown in FIG. 6A.

As the movable handle 34 moves from the first position shown in FIGS. 5A and 5B toward the second position shown in FIG. 6A and FIG. 6B, the rod 192 enters into the concave groove 178c. Therefore, the coil 38a of the torsion spring 38 is pressed onto the first inclined surface 178a, and moves from the first body 32a side to the second body 32b side along the rod 192. At this time, along the first inclined surface 178a, the coil 38a of the torsion spring 38 slides from the proximal side toward the distal side, and slides from the first body 32a side toward the second body 32b side. Furthermore, the contact position of the end portion 39b of the second arm 38c of the torsion spring 38 with respect to the second inclined surface 178b changes (shifts).

The opening angle between the first arm 38b and the second arm 38c of the torsion spring 38 is smaller as the movable handle 34 moves from the first position toward the second position. Therefore, the biasing force against the second inclined surface 178b by the torsion spring 38 increases as the movable handle 34 moves from the first position to the second position.

The end portion 39b of the torsion spring 38 slides on the second inclined surface 178b from the position shown in FIG. 5B to the position shown in FIG. 6B. The opening angle between the first arm 38b and the second arm 38c of the torsion spring 38 at the second position in this case is greater than the opening angle between the first arm 38b and the second arm 38c of the torsion spring 38 when the end portion 39b of the torsion spring 38 does not slide on the second inclined surface 178b from the position shown in FIG. 5B. Therefore, in the present embodiment, when the movable handle 34 moves from the first position to the second position, the biasing force F of the torsion spring 38 is reduced rather than linearly increased.

In the present embodiment, biasing force F1 of the torsion spring 38 of the component in the direction orthogonal to the contact surface 80 by the end portion 39b of the second arm 38c when the movable handle 34 is in the first position, and distance L1 of the movable handle 34 from the rotation shaft 62 to the position orthogonal to the direction of the biasing force F1, are set. At the first position, moment (grip force amount) M1 of force around the axis of the rotation shaft 62 can be expressed as M1=F1dL1.

Biasing force F2 of the torsion spring 38 of the component in the direction orthogonal to the contact surface 80 by the end portion 39b of the second arm 38c when the movable handle 34 is in the second position, and distance L2 of the movable handle 34 from the rotation shaft 62 to the position orthogonal to the direction of the biasing force F2, are set. At the second position, moment (grip force amount) M2 of force can be expressed as M2=F2dL2.

At this time, the biasing force F1 is smaller than the biasing force F2, while the distance L1 is smaller than the distance L2. Therefore, the moment M may increase from the first position toward the second position.

Assuming that the end portion 39b of the torsion spring 38 does not move on the second inclined surface 178b at the first position and the second position, virtual biasing force Fa of the torsion spring 38 of the component in a direction orthogonal to the contact surface 80 by the end portion 39b of the second arm 38c at the second position, and distance La of the movable handle 34 from the rotation shaft 62 to the position orthogonal to the biasing force Fa, are set. Moment (grip force amount) Ma of virtual force can be expressed as Ma=FadLa. At this time, the biasing force F2 is smaller than the biasing force Fa, while the distances La and L2 are substantially the same. Therefore, the moment M2 is smaller than the moment Ma.

Therefore, while the grip force amount of the movable handle 34 required by the surgeon may increase from the first position toward the second position, the surgeon can perform the operation of gripping the movable handle 34 with respect to the fixed handle 44 with a small possible force (force amount). Therefore, according to the present embodiment, it is possible to provide a medical instrument 10 in which a surgeon can easily perform the gripping operation of the movable handle 34 while the spring 36 maintains the biasing force separating the movable handle 34 relative to the housing 32.

The surgeon releases the grip of the movable handle 34 with respect to the fixed handle 44, and shifts the position of the movable handle 34 from the second position to the first position, thereby releasing the treated living tissue. At this time, the biasing force F2 of the torsion spring 38 moves the coil 38a with respect to the rod 192 from the position shown in FIG. 6A to the position shown in FIG. 5B (from the position apart from the first body 32a to the position close to the first body 32a), and moves the end portion 39b of the second arm 38c with respect to the second inclined surface 178b from the position shown in FIG. 6A to the position shown in FIG. 5B. Accordingly, the movable handle 34 moves from the second position to the first position, and the living tissue treated is released from among the pair of jaws 24a and 24b of the end effector 24.

Another exemplary embodiment will be described with reference to FIGS. 7 and 8.

Figure 7:
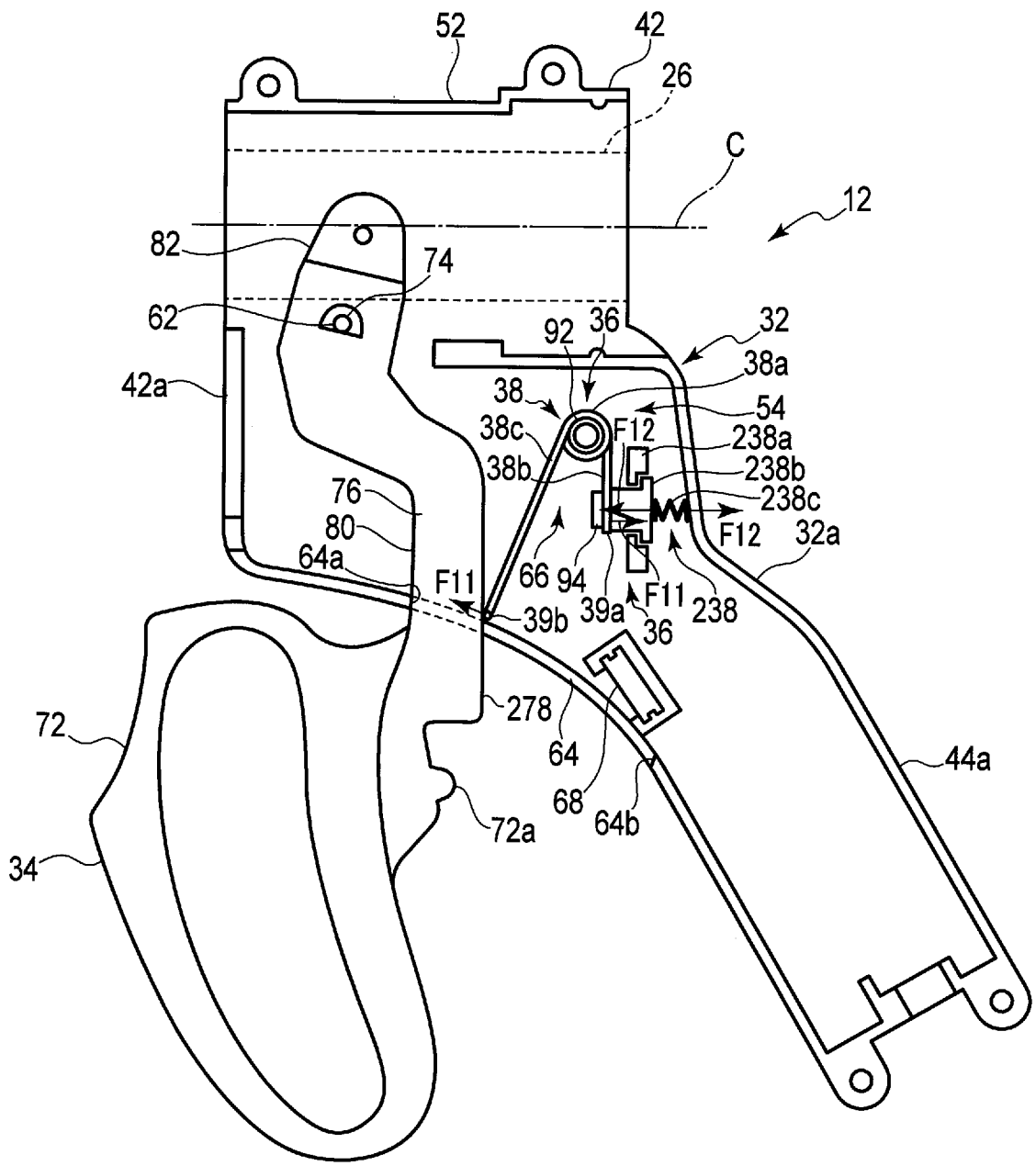
FIG. 7 is a schematic view showing a state in which, while a movable handle and a spring are arranged in a first body of a housing of a handle assembly of a medical instrument according to a third embodiment, a finger hook portion of the movable handle is set apart from a grip of the housing.

As shown in FIG. 7, the spring 36 includes a torsion spring 38. The housing 32 includes an auxiliary spring 238.

The auxiliary spring 238 includes a frame 238a provided in a fixed manner by being integrated with the arrangement portion 54, a pressing member 238b fitted to the frame 238a, and a compression coil spring 238c provided between the pressing member 238b and the rear portion of the first body 32a. The frame 238a cooperates with the torsion spring 38 and the compression coil spring 238c to allow the pressing member 238b to move in a predetermined direction within a predetermined range.

The end portion 39a of the first arm 38b of the torsion spring 38 is supported between the support portion 94 and the pressing member 238b. Therefore, the end portion 39a of the first arm 38b of the torsion spring 38 is supported by the housing 32. The second arm 38c of the torsion spring 38 is slidably supported by the support surface 278 of the rear surface of the connecting portion 76 of the movable handle 34. In the present embodiment, the support surface 278 is formed as a planar surface (inclined surface), but the support surface 78 described in the first embodiment may be used.

At the first position shown in FIG. 7, biasing force F11 (a component in the direction orthogonal to the second arm 38c) at the end portion 39b of the torsion spring 38 in the direction orthogonal to the second arm 38c of the torsion spring 38 is, for example, approximately 3 N to 5 N. Similarly, biasing force (a component in the direction orthogonal to the first arm 38b) F11 at the end portion 39a of the torsion spring 38 in the direction orthogonal to the first arm 38b of the torsion spring 38 is, for example, approximately 3 N to 5 N. The compression coil spring 238c applies force F12 greater than the torsion spring 38, e.g., 6 N or more, toward the proximal side (rear side) of the first body 32a. Therefore, when the movable handle 34 is in the first position, the pressing member 238b is fitted into the frame 238a, and the end portion 39a of the first arm 38b of the torsion spring 38 is urged toward the support portion 94.

As the movable handle 34 moves from the first position toward the second position, the end portion 39b of the second arm 38c slides along the support surface (planar surface) 278. At the second position shown in FIG. 8, the opening angle between the first arm 38b and the second arm 38c of the torsion spring 38 is smaller, and therefore, biasing force F21 (component in the direction orthogonal to the second arm 38c) greater than the biasing force F11, e.g., approximately 7 N, applies. The biasing force F22 of 7 N or so, for example, is applied to the compression coil spring 238c as well.

In order to prevent the opening angle between the first arm 38b and the second arm 38c of the torsion spring 38 from becoming as small as possible, the coil 38a of the torsion spring 38 rotates around the boss 92. Since the end portion 39a of the first arm 38b is a free end, the end portion 39a of the first arm 38b keeps away from the support portion 94. The end portion 39a of the first arm 38b presses the pressing member 238b against the biasing force of the compression coil spring 238c, and therefore, the pressing member 238b is disengaged from the frame 238a and keeps away from the frame 238a.

In this manner, the opening angle between the first arm 38b and the second arm 38c of the torsion spring 38 becomes smaller as the movable handle 34 moves from the first position to the second position, and the biasing force F becomes gradually larger, but the auxiliary spring 238 acts to alleviate an increase in the biasing force of the torsion spring 38. In particular, in response to the movable handle 34 moving from the first position to the second position, the contact position between the pressing member 238b and the end portion 39a of the first arm 38b of the torsion spring 38 moves relatively to the side on which the biasing force F21 is applied to the housing 32 (side to which the pressing member 238b moves). Therefore, while the grip force amount required by the surgeon may increase from the first position toward the second position, the surgeon can perform the operation of gripping the movable handle 34 with respect to the fixed handle 44 with a small possible force (force amount). Therefore, according to the present embodiment, it is possible to provide a medical instrument 10 in which a surgeon can easily perform the gripping operation of the movable handle 34 while the spring 36 keeps the movable handle 34 away from the housing 32 by means of the biasing force.

Figure 8:
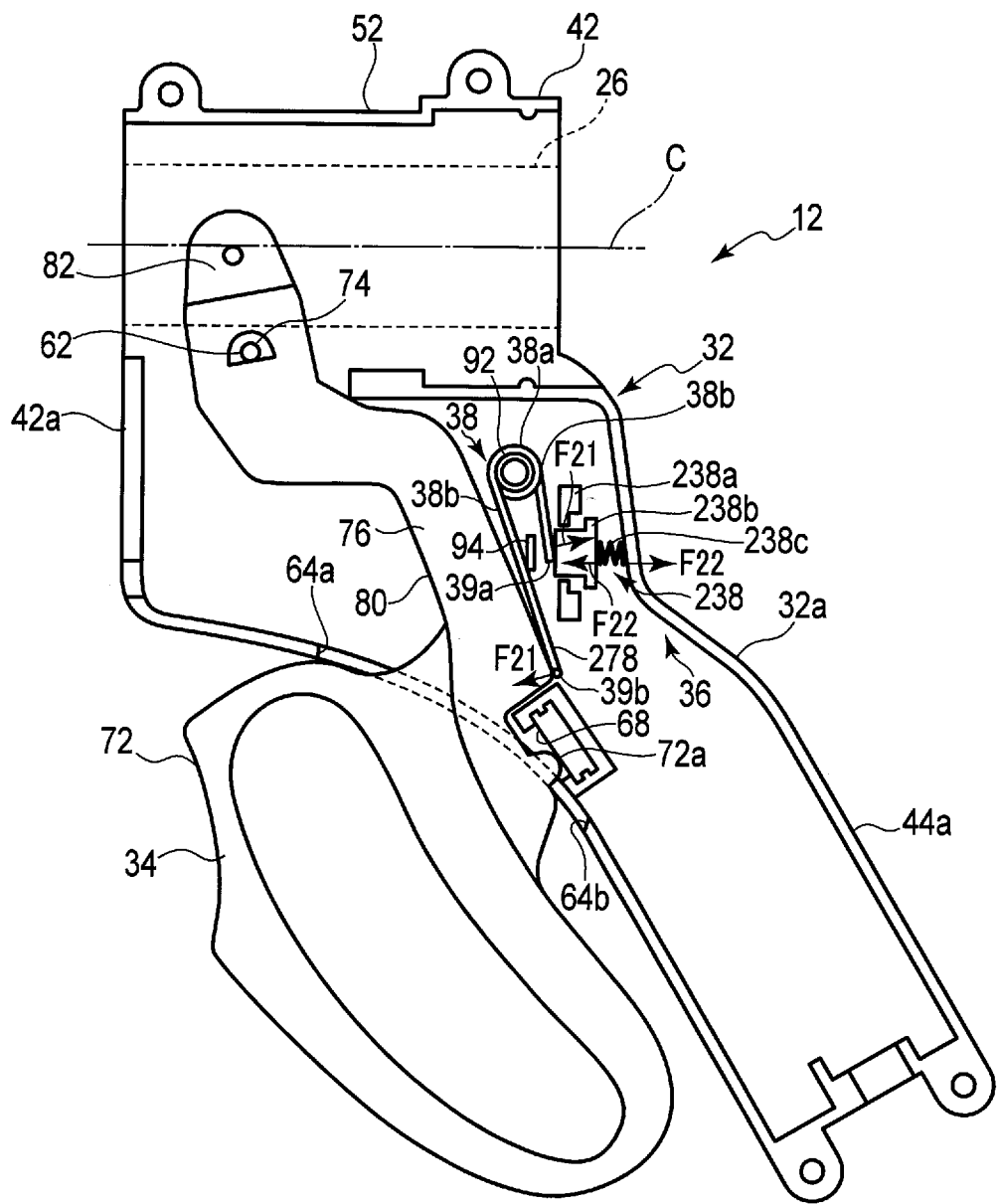
FIG. 8 is a schematic view showing a state in which the finger hook portion of the movable handle is brought to a position close to the grip of the housing shown in FIG. 7.

Instead of the support surface 278 shown in FIGS. 7 and 8, the support surface 78 described in the first embodiment may be used as a matter of course.

For the auxiliary spring 238, it is also preferable to use other types of spring (e.g., leaf spring) other than the compression coil spring.

Another exemplary embodiment will be described with reference to FIGS. 9 and 10. Here, an example will be described which involves the use of, as a spring 36, a compression coil spring 338 arranged at an outer periphery of a later-described rod 392, instead of the torsion spring 38.

The spring support portion 66 includes a rod 392, a first support portion 394a that is provided in the first body 32a of the housing 32 and supports the proximal end of the rod 392, and a second support portion 394b that supports the distal end of the rod 392. The first support portion 394a is supported by, for example, the rear surface of the first body 32a of the housing 32. The second support portion 394b is supported by, for example, the front surface of the first body 32a of the housing 32.

The connecting portion 76 includes an insertion portion 376 such as a through hole or concave groove penetrating between the contact surface 80 on the front surface and the support surface 78 on the rear surface. If the insertion portion 376 is formed as a concave groove, when the support surface 78 is viewed from the proximal side (rear side), the insertion portion 376 has a substantially U-shaped edge, and is open toward the arrangement portion 54 side.

One end (proximal end) 339a of the compression coil spring 338 is supported by the first support portion 394a. The other end (distal side) 339b of the compression coil spring 338 is supported by the support surface 78 of the rear surface of the connecting portion 76.

Figure 9:
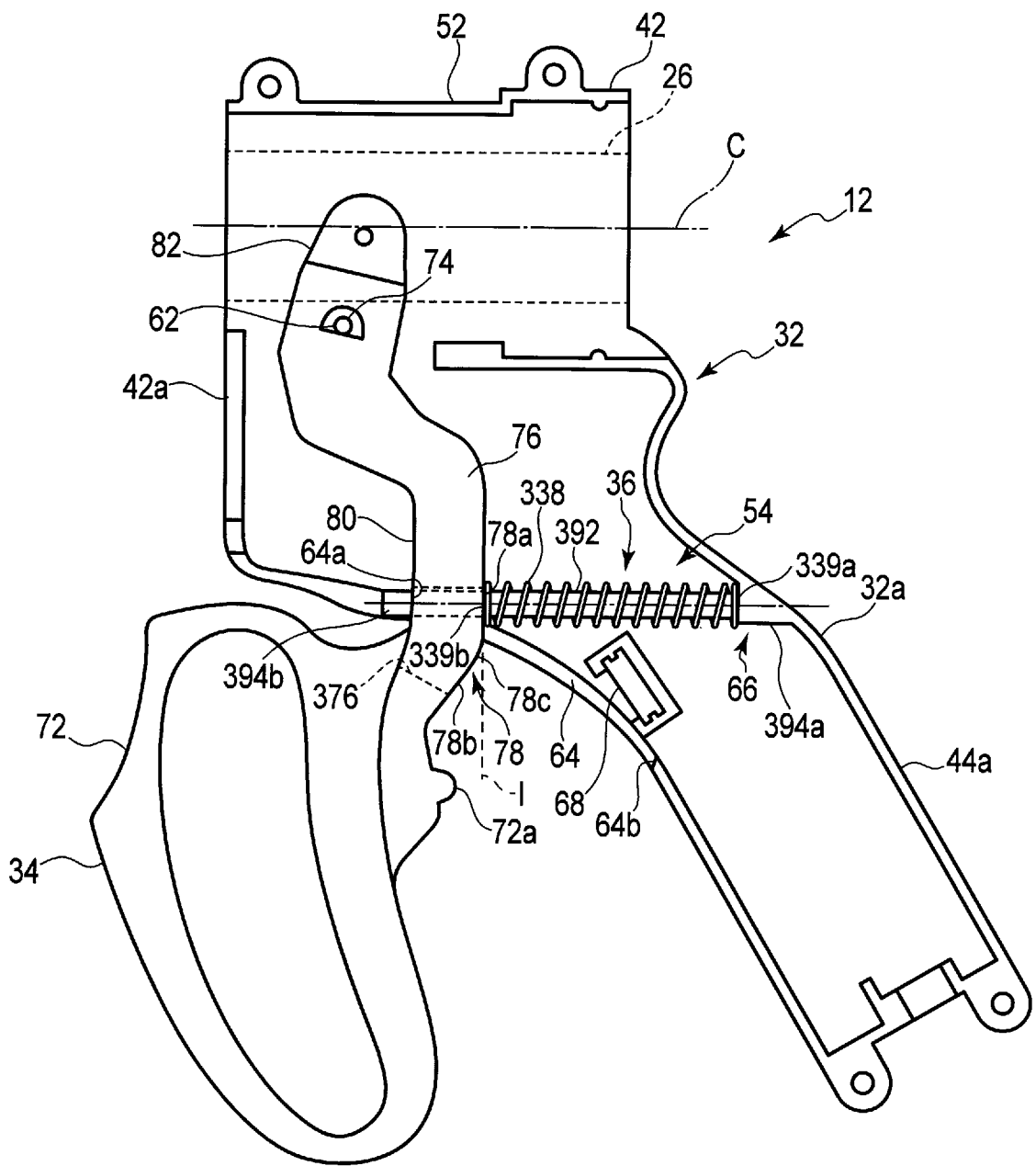
FIG. 9 is a schematic view showing a state in which, while a movable handle and a spring are arranged in a first body of a housing of a handle assembly of a medical instrument according to a fourth embodiment, a finger hook portion of the movable handle is set apart from a grip of the housing.

As shown in FIG. 9, when the movable handle 34 is in the first position, the distal end of the compression coil spring 338 is in contact with the planar surface 78a of the support surface 78. As shown in FIG. 10, when the movable handle 34 is in the second position, the distal end of the compression coil spring 338 is in contact with the inclined surface 78b of the support surface 78.

By forming the support surface 78 of the connecting portion 76 as described above, in the same manner as described in the first embodiment, it is possible to reduce the biasing force of the compression coil spring 338 at the second position or the vicinity thereof as compared when the support surface 78 is formed by only the planar surface.

Specifically, in response to the movable handle 34 moving from the first position to the second position, the contact position between the end 339b of the compression coil spring 338 and the support surface 78 of the movable handle 34, particularly when at the curved surface 78c and the inclined surface 78b, shifts to a side where the biasing force is applied (front side of the handle assembly 12). Therefore, when the end portion 339b of the compression coil spring 338 slides along the inclined surface 78b, an increase in the biasing force exerted by the end portion 339b of the compression coil spring 338 is suppressed as compared to when the planar surface 78a is continuous, as indicated by the dashed line I.

Therefore, the surgeon can perform the operation of gripping the movable handle 34 relative to the fixed handle 44 with a lower force (force amount) as compared to when it is assumed that the support surface 78 is formed only by the planar surface. Therefore, according to the present embodiment, it is possible to provide a medical instrument 10 in which a surgeon can easily perform the gripping operation of the movable handle 34 while the spring 36 maintains the biasing force separating the movable handle 34 relative the housing 32.

Another exemplary embodiment will be described with reference to FIGS. 11 and 12. Here, an example will be described which involves the use of, as a spring 36, a tension coil spring 438a arranged at an outer periphery of a later-described rod 492 instead of the torsion spring 38.

The spring support portion 66 includes a rod 492, a first support portion 494a that is provided in the first body 32a of the housing 32 and supports the distal end of the rod 492, and a second support portion 494b that supports the proximal end of the rod 492. The first support portion 494a is supported by, for example, the front of the first body 32a of the housing 32. The second support portion 494b is, for example, integrated with the arrangement portion 54 of the first body 32a of the housing 32, or supported by the rear surface of the first body 32a.

The connecting portion 76 includes an insertion portion 476 such as a through hole or groove penetrating between the contact surface 80 on the front and the support surface 78 on the rear. If the insertion portion 476 is formed as a concave groove, when the support surface 78 is viewed from the proximal side, the insertion portion 476 is formed at a substantially U-shaped edge and is opened toward the arrangement portion 54 side.

The connecting portion 76 further includes a support groove 478 on the side surface 84. The support groove 478 includes a straight groove 478a corresponding to the planar surface 78a of the support surface 78 described in the first embodiment, an inclined groove 478b corresponding to the inclined surface 78b, and a curved groove 478c corresponding to the curved surface 78c and between the straight groove 478a and the curved groove 478b. The straight groove 478a has a pair of planar surfaces (first inclined surface). It is preferable that the pair of planar surfaces of the straight groove 478a be parallel to each other. The inclined groove 478b has a pair of inclined surfaces (second inclined surface). It is preferable that the pair of inclined surfaces of the inclined groove 478b be parallel to each other. The curved groove 478c has a pair of curved surfaces. It is preferable that the pair of curved surfaces of the curved grooves 478c be parallel to each other.

One end (distal end) of the tension coil spring 438a is fixed to (supported by) a first support portion 494a of the spring support portion 66. A hook 438b is integrally formed at the other end (proximal end) of the tension coil spring 438a. A pin (slider) 438c extending in a direction orthogonal to the longitudinal axis C is fixed to the hook 438b. The pin 438c is movable along the support groove 478.

Figure 11:
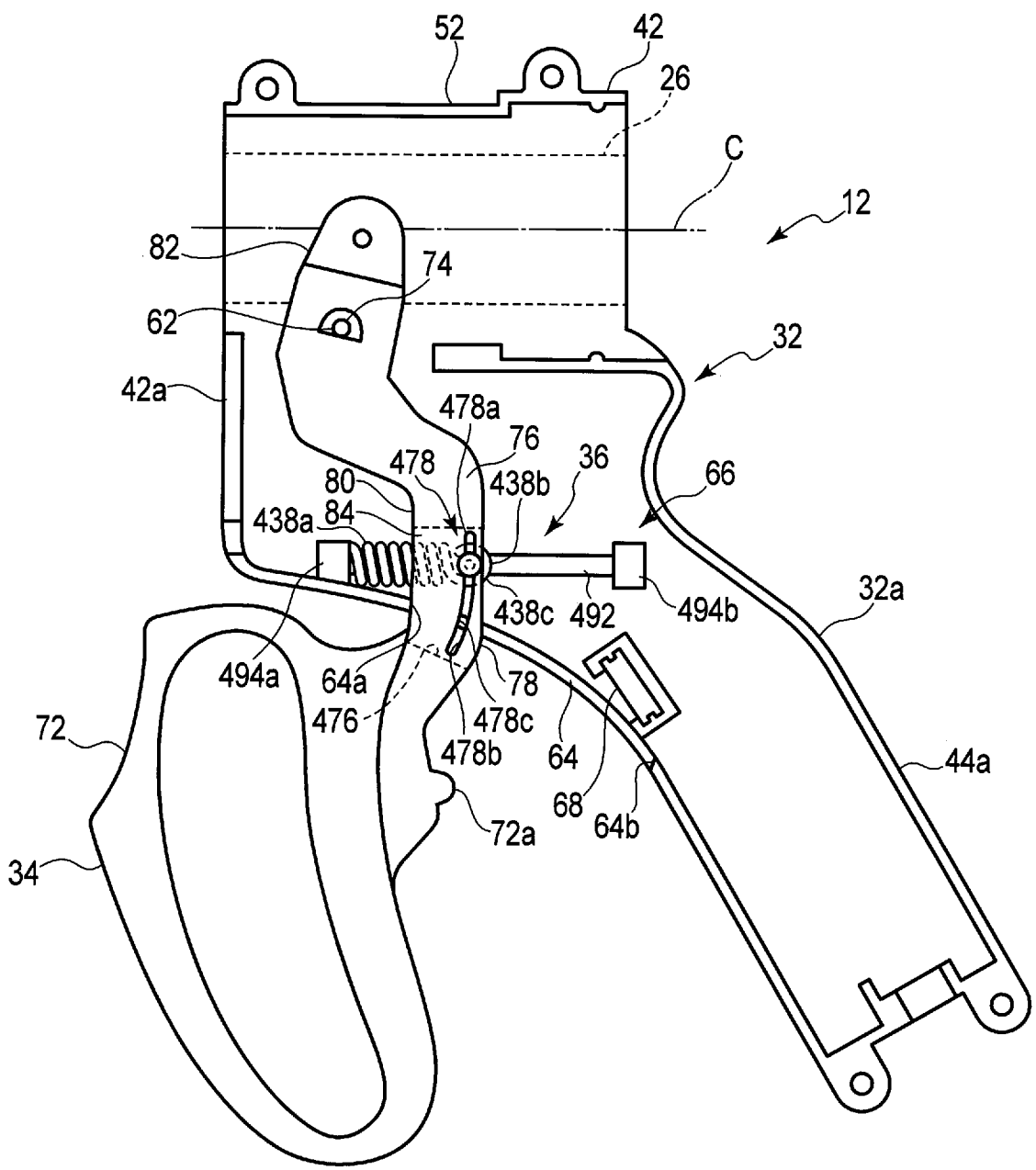
FIG. 11 is a schematic view showing a state in which, while a movable handle and a spring are arranged in a first body of a housing of a handle assembly of a medical instrument according to a fifth embodiment, a finger hook portion of the movable handle is set apart from a grip of the housing.
Figure 12:
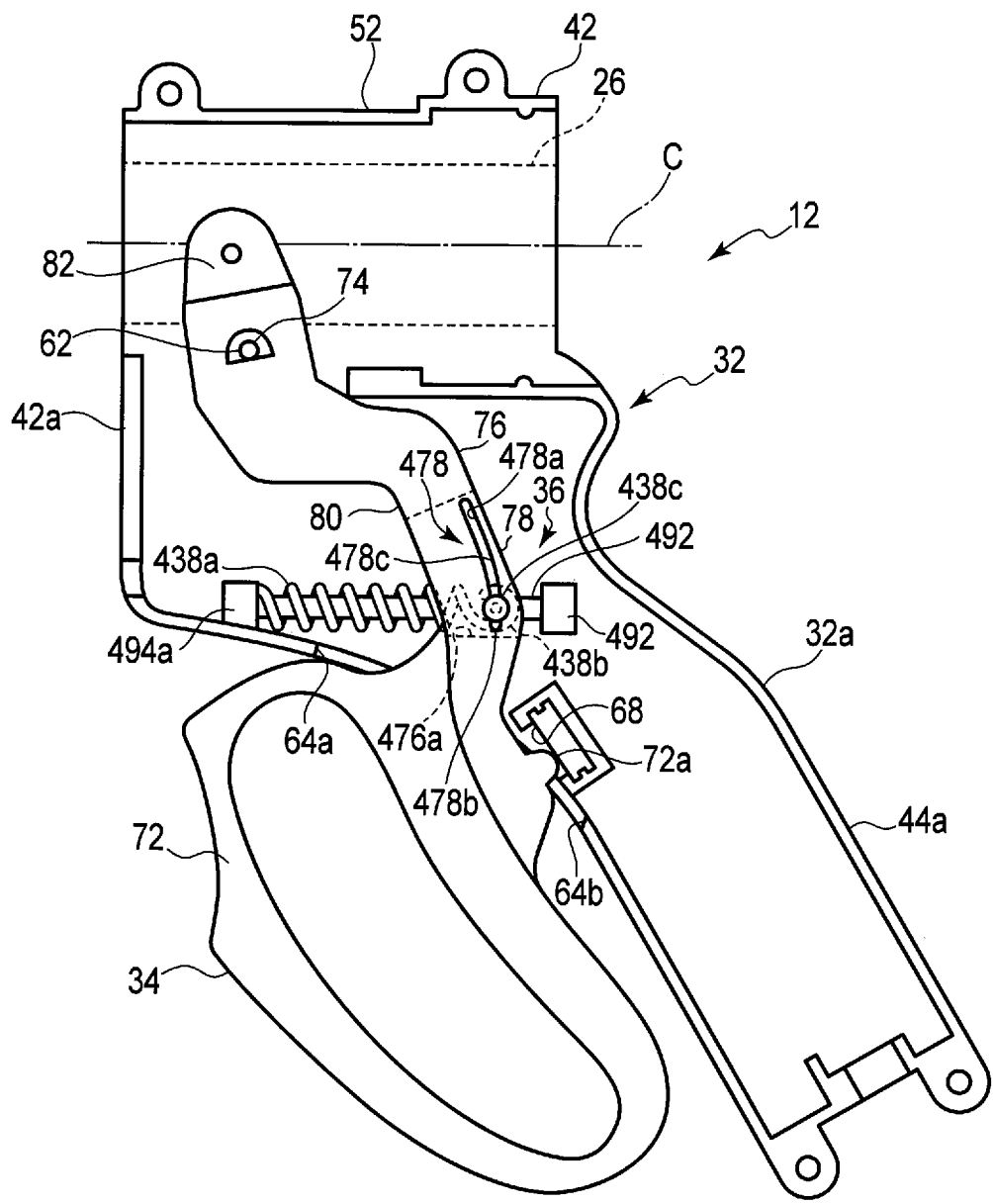
FIG. 12 is a schematic view showing a state in which the finger hook portion of the movable handle is brought to a position close to the grip of the housing shown in FIG. 11.

As shown in FIG. 11, when the movable handle 34 is in the first position, the pin 438c fixed to the hook 438b of the tension coil spring 438a is arranged in the straight groove 478a of the support groove 478. As shown in FIG. 12, when the movable handle 34 is in the second position, the pin 438c of the tension coil spring 438a is arranged in the inclined groove 478b of the support groove 478.

By forming the support groove 478 of the connecting portion 76 as described above, in the same manner as described in the first embodiment, it is possible to reduce the biasing force of the tension coil spring 438a at the second position or in the vicinity thereof as compared when the support groove 478 is formed to be only straight.

Specifically, in response to the movable handle 34 moving from the first position to the second position, the contact position between the pin 438c of the tension coil spring 438a and the support groove 478 of the movable handle 34, particularly at the curved groove 478c and the inclined groove 478b, shifts to a side where the biasing force is applied (front side of the handle assembly 12). Therefore, when the pin 438c of the tension coil spring 438a slides along the inclined groove 478b, an increase in the biasing force by the tensile coil spring 438a is suppressed as compared to when the straight groove 478a is continuous (not shown) in the same manner as shown by the dashed line I in FIG. 3.

Therefore, the surgeon can perform the operation of gripping the movable handle 34 relative to the fixed handle 44 with a lower force (force amount) as compared to when it is assumed that the support surface 78 is formed only by the planar surface. Therefore, according to the present embodiment, it is possible to provide a medical instrument 10 in which a surgeon can easily perform the gripping operation of the movable handle 34 while the spring 36 keeps the movable handle 34 away from the housing 32 by means of the biasing force.

In the handle assembly 12 shown in FIGS. 1 to 12, the movable handle 34 is arranged at the distal side (front side) of the fixed handle 44. The handle assembly 12 may have a movable handle 34 fixed to the proximal side (rear side) of the fixed handle 44. In other words, in the first to fifth embodiments, an example has been explained in which the finger hook portion 72 of the movable handle 34 is arranged at the distal side (front side) of the fixed handle 44. The finger hook portion 72 of the movable handle 34 is not limited to being arranged at the distal side of the fixed handle 44, and may be arranged at the proximal side (rear side) as publicly known. Even in this case, the movable handle 34 is movable around the axis of the rotation shaft 62 between the first position, in which it is set apart from the fixed handle 44, and the second position in which it is closer to the fixed handle 44. By employing appropriate structure of the first to fifth embodiments, an increase in the biasing force F of the spring 36 can be effectively suppressed when the movable handle 34 moves from the first position to the second position.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A medical instrument comprising:
    a housing;
    a fixed handle;
    a movable handle that is configured to move relative to the fixed handle, the movable handle being configured to move from a first position to a second position in a direction towards the fixed handle, the second position being a position of the movable handle that is closest to the fixed handle; and
    a spring provided between the housing and the movable handle and configured to apply a biasing force to the movable handle, the medical instrument being configured to control the biasing force generated in the spring when the movable handle moves from the first position to the second position, wherein:
the medical instrument is configured such that:
the biasing force of the spring against the movable handle increases as the movable handle moves from the first position to the second position, and the biasing force of the spring in the first position is less than the biasing force of the spring in the second position, and
as the movable handle moves from the first position to the second position, an amount of increase in the biasing force generated in the spring decreases when the spring is closer to the second position than the first position, and
the movable handle is configured to move from the second position to the first position with respect to the fixed handle by the biasing force of the spring when a surgeon releases a grip of the movable handle with respect to the fixed handle.

2. The medical instrument according to claim 1, wherein: the movable handle includes:
a rotation support point portion supported by a rotation shaft;
a finger hook portion configured to allow the surgeon to hook a finger; and
a connecting portion provided between the rotation support point portion and the finger hook portion, the biasing force of the spring being applied to the connecting portion.

3. The medical instrument according to claim 2, wherein the movable handle further includes a support surface which is formed on a proximal side of the connecting portion, wherein the spring is configured to contact the support surface of the movable handle.

4. The medical instrument according to claim 2, wherein the movable handle further includes a support groove which is formed in the connecting portion, wherein the support groove is configured to receive the biasing force of the spring.

5. The medical instrument according to claim 1, wherein the housing includes a support portion that supports one end of the spring.

6. The medical instrument according to claim 1, wherein:
the movable handle includes a support surface, the biasing force of the spring being applied to the support surface, and
the support surface includes an inclined surface such that as the movable handle moves from the first position to the second position, a position of contact between an end portion of the spring and the support surface is shifted relative to the support surface in a direction of the biasing force.

7. The medical instrument according to claim 6, wherein:
as the movable handle pivots around a rotation shaft and moves from the first position to the second position, an increase in a moment of force around the rotation shaft of the movable handle is suppressed as compared to if the contact position of the end portion of the spring on the support surface did not shift in a direction of the biasing force when the movable handle moves from the first position to the second position; and
the moment is determined based on the biasing force applied against the movable handle at the end portion of the spring and a distance from the rotation shaft to a position that intersects a direction of the biasing force at a right angle.

8. The medical instrument according to claim 6, wherein:
the support surface further includes a planar surface, and the inclined surface is inclined relative to the planar surface, and
as the movable handle moves from the first position to the second position, the end portion of the spring is configured to slide from the planar surface to contact the inclined surface to suppress an increase in the biasing force generated in the spring as compared to if the end portion of the spring continued to slide along the planar surface during movement of the movable handle from the first position to the second position.

9. The medical instrument according to claim 8, wherein the support surface includes a curved surface that connects the planar surface and the inclined surface.

10. The medical instrument according to claim 6, wherein:
as the movable handle moves from the first position to the second position, the end portion of the spring is configured to slide on the inclined surface to suppress an increase in the biasing force generated in the spring as compared to if the support surface did not include the inclined surface.

11. The medical instrument according to claim 6, further comprising an auxiliary spring in addition to the spring,
wherein as the movable handle moves from the first position to the second position, the auxiliary spring is configured to act to suppress an increase in the biasing force generated in the spring as compared to if the medical instrument did not include an auxiliary spring.

12. The medical instrument according to claim 6, wherein:
the support surface includes a straight groove, and an inclined groove inclined with respect to the straight groove,
the end portion of the spring is provided with a slider that is configured to move along the straight groove and the inclined groove, and
as the movable handle moves from the first position to the second position, the slider is configured to move along the inclined groove from the straight groove to suppress an increase in the biasing force generated in the spring as compared to if the support surface did not include the inclined groove.

13. The medical instrument according to claim 12, wherein the support surface includes a curved groove formed by a curved surface between the straight groove and the inclined groove.

14. The medical instrument according to claim 1, wherein the spring is a torsion spring.

15. The medical instrument according to claim 1, wherein the movable handle is configured to move to open and close a jaw configured to grasp a living tissue.

16. The medical instrument according to claim 15, wherein an end effector including the jaw is configured to supply treatment energy to the living tissue to perform treatment.

17. The medical instrument according to claim 16, wherein the treatment energy is any one of ultrasonic energy, high frequency energy, or thermal energy.

18. The medical instrument according to claim 1, wherein:
the spring includes a first end portion which supports the housing, and a second end portion which contacts the movable handle, and
the second end portion is formed into an L shape.

19. The medical instrument according to claim 18, wherein:
- the movable handle includes a support surface including a planar surface and an inclined surface that is inclined relative to the planar surface, and
- as the movable handle moves from the first position to the second position, the second end portion of the spring is configured to slide from the planar surface to the inclined surface such that the second end portion is in contact with the inclined surface in the second position.

20. The medical instrument according to claim 1, wherein movement of the movable handle between the first position and the second position is a maximum movement range of the movable handle relative to the fixed handle.

\* \* \* \* \*